(12) United States Patent
Fuhrmann et al.

(10) Patent No.: US 7,230,131 B2
(45) Date of Patent: Jun. 12, 2007

(54) CARNITINE-MAGNESIUM HYDROXYCITRATE

(75) Inventors: Martin Fuhrmann, Gelterkinden (CH); Daniel Pianzola, Brig-Glis (CH)

(73) Assignee: Lonza AG, Basel (CH)

( * ) Notice: Subject to any disclaimer, the term of this patent is extended or adjusted under 35 U.S.C. 154(b) by 241 days.

(21) Appl. No.: 10/785,013

(22) Filed: Feb. 25, 2004

(65) Prior Publication Data

US 2004/0167219 A1    Aug. 26, 2004

Related U.S. Application Data

(62) Division of application No. 10/362,730, filed as application No. PCT/EP01/09962 on Aug. 29, 2001, now abandoned.

(30) Foreign Application Priority Data

Aug. 29, 2000 (EP) .................................. 00118656

(51) Int. Cl.
*C07C 59/245* (2006.01)
*C07C 59/265* (2006.01)

(52) U.S. Cl. ...................................... 562/582; 562/584

(58) Field of Classification Search ................ 562/512, 562/553, 567, 590
See application file for complete search history.

(56) References Cited

U.S. PATENT DOCUMENTS

| 4,602,039 | A |  | 7/1986 | Cavazza |
|---|---|---|---|---|
| 5,071,874 | A | * | 12/1991 | Scholl et al. ................ 514/561 |
| 5,783,603 | A |  | 7/1998 | Majeed et al. |
| 6,051,608 | A |  | 4/2000 | Santaniello et al. |
| 6,217,898 | B1 | * | 4/2001 | Cavazza ...................... 424/450 |
| 6,337,349 | B2 | * | 1/2002 | Scafetta et al. .............. 514/547 |
| 2001/0011081 | A1 | * | 8/2001 | Claudio ........................ 514/77 |

FOREIGN PATENT DOCUMENTS

| EP | 0402755 | 12/1990 |
|---|---|---|
| GB | 1153640 | 4/1967 |

OTHER PUBLICATIONS

Lewis, Y., et al., Phytochemistry, (1965), 4, pp. 619-625.

* cited by examiner

*Primary Examiner*—Thurman Page
*Assistant Examiner*—Karl Puttlitz
(74) *Attorney, Agent, or Firm*—Fisher, Christen & Sabol

(57) ABSTRACT

A method for preparing, from at least one hygroscopic substance, mixtures that can be granulated and that have little hygroscopicity. The corresponding mixtures, especially carnitine-magnesium citrate and carnitine-magnesium hydroxycitrate, are produced.

19 Claims, No Drawings

CARNITINE-MAGNESIUM HYDROXYCITRATE

The application is a division of U.S. Ser. No. 10/362,730, filed on May 14, 2003, now abandoned, that is a 371 U.S. national stage application of International Patent Application PCT/EP01/109962, filed on Aug. 29, 2001, that has priority benefit of European Patent Application No. 00118656.8, filed on Aug. 29, 2000.

The present application relates to a novel method for preparing a mixture which can be granulated and which is suitable for pharmaceutical dosage forms or for dietary supplementation, comprising at least one hygroscopic substance, preferably L-carnitine. The application further relates to such novel mixtures that can be granulated, comprising salts of carnitine, at least one alkali metal or alkaline earth metal cation, and an organic, physiologically acceptable acid. The present invention further relates to a carnitine-magnesium hydroxycitrate.

L-(−)-Carnitine plays an important part in energy metabolism, in the breakdown of fatty acids, in the eukaryotic organism. It is a vitamin-like substance which has been admixed to food products or administered as dietary supplement or pharmaceutical dosage form for some time to prevent and treat manifestations of deficiency. Such manifestations of deficiency may occur in particular in children and elderly people or when the diet is unbalanced. Magnesium and citrate are likewise physiological substances; manifestations of deficiency due to inadequate intake of magnesium in particular are not rare. They can be prevented by taking Mg products. Citrate is utilized without difficulty in energy metabolism. The muscle tissue of a healthy adult contains approximately 20 g of magnesium and 20 g of L-carnitine. A healthy adult can take about 2 g of L-carnitine additionally each day for optimal energy supply. Since carnitine and magnesium are required for metabolic processes which are closely associated, a combination product has a beneficial synergistic effect.

It is well known that L-carnitine is very hygroscopic. This is the cause of a lack of storability of the solid substance and of simple powder mixtures prepared therefrom, and causes problems such as inadequate flowability during the further processing of pure solid carnitine or powdered mixtures containing carnitine in the human food, animal feed or drugs industry.

EP 402 755 describes the stoichiometric complex salt L-carnitine-magnesium citrate which is distinctly less hygroscopic than free carnitine and is thus stable on storage. At a relative humidity of 56%, the water uptake by the complex salt after storage for 1 week is 21% by weight. The complex salt is prepared by mixing the components in aqueous solution at 60° C. The solid is then obtained by spray drying or crystallization. The residual hygroscopicity of the carnitine-magnesium citrate prepared in this way still proves to be a certain problem during storage and further processing. A further reduction is desirable.

Salts which, besides carnitine, comprise exclusively hydroxy acids such as, for example, tartaric acid, without involvement of metal ions, and which are in a similar way less hygroscopic than pure carnitine are also known. All known methods of preparation without exception require the use of relatively large amounts of water or aqueous solvents and, for the crystallization, also organic solvents. The drying methods, e.g. spray drying, require a considerable energy input or the use of organic solvents. The latter is associated with additional costs and the problem of disposal of the waste solvents.

It is the object of the present invention to avoid this and other disadvantages of the prior art.

This object is achieved by the method of preparation of the invention, and by the mixtures and salts of the invention.

In one method of the invention for preparing a mixture that can be granulated for dietary supplementation or pharmaceutical use, where the mixture comprises at least one hygroscopic substance, preferably L-carnitine, in a first stage the solid hygroscopic substance is mixed with at least one organic acid and at least one metal hydroxide without addition of water or with addition of not more than 15% by weight of water, and in a second, subsequent stage the water content of the resulting mixture is reduced by drying to below 5% by weight, with the resulting composition preferably remaining viscous and, where appropriate, being solidified in a further step of the method.

Addition of water means in this connection for the purposes of the present invention the water added in liquid form to the mixture in its entirety, excluding the water of reaction from the neutralization reaction between acid and hydroxide. It can be added as separate liquid, but it can also serve as solvent or suspending agent for example for the acid or the hydroxide; such a solution or suspension can then be added to the mixing process. In this sense, the organic acid and the metal hydroxide are starting substances which are solid per se and which add to the mixture no additional water apart from water of crystallization which is possibly present.

Solid starting substances mean for the purposes of the present invention preferably free-flowing substances which are in the form of coarse granules or fine powder. A hygroscopic substance means for the purposes of the present invention a substance which on storage under standard conditions is prone to conglutination or deliquescence through uptake of water. In particular, substances which on storage at a relative humidity of 56% under standard conditions show a weight gain of more than 20% after 1 week are regarded as hygroscopic substances within the meaning of the present application. Examples of such hygroscopic substances are carnitine and creatine, which bind moisture strongly. However, a further possibility is the salt or derivative of such a hygroscopic compound, for example carnitine chloride or an alkanoylcarnitine, in particular acetylcarnitine. For the purposes of the present invention, carnitine or alkanoylcarnitine is preferably in the physiological L-(−) form, However, it is also possible to use racemic DL-carnitine. An organic acid or an acid residue means in the sense of the present application in particular physiologically acceptable, monobasic or polybasic organic acids, in particular biogenic hydroxy acids or fruit acids and their derivatives such as, for example, ascorbic acid (vitamin C), tartaric acid, malic acid, pyruvic acid, hydroxypyruvic acid, fumaric acid, glutaric acid, citric acid, (−)-hydroxycitric acid or isocitric acid, aspartic acid, glutamic acid, succinic acid, as are customary and approved for example in effervescent tablets and for use in food products or medicaments. A metal hydroxide means for the purposes of the present invention preferably those hydroxides which are in solid form, for example alkali metal hydroxides or, in a particularly preferred embodiment, alkaline earth metal hydroxides. The alkaline earth elements are expediently physiologically acceptable, such as calcium or magnesium, which occur in the mammalian organism in considerable quantity.

A composition which can be granulated and has been prepared by the method of the invention is surprisingly distinguished by a particularly low hygroscopicity compared with the starting substance, for example pure carnitine. A further advantage of the method of the invention is the avoidance of the addition of large amounts of water, so that eventually costly removal of the residual moisture from the final product is necessary, and the simple manner of preparation which requires no additional processing steps.

The use of a metal hydroxide together for example with citric acid or another organic acid leads in a neutralization reaction advantageously and directly to an optimal distribution of the water of reaction from the neutralization between the solids particles, and thus permits minimization of the addition of water and suitable flow properties of the powdered or pasty composition. In a preferred embodiment, the content of added water in the mixture is not more than 3%, and in a particularly preferred embodiment is not more than 1% by weight, and in the most preferred embodiment no additional water is admixed. There is merely in situ formation of a small amount of water, depending on the mixing ratios, through the neutralization reaction. The effect of this according to the invention is faster drying and lower hygroscopicity of the solid product.

It is also possible to admix other substances such as stabilizers, other active ingredients, pharmaceutical carriers or fillers, waxes, desiccants, colors and the like to the mixture. The method of the invention is also suitable in particular for preparing mixtures of solids which are of low compatibility in relation to their solubility characteristics, e.g. hydrophobic and hydrophilic substances such as, for example, carnitine on the one hand and lipid-soluble vitamins or vitamin-like substances such as vitamin E or coenzyme Q on the other hand.

It is possible to use for mixing the solid starting substances the mixing apparatuses known per se to the skilled worker, such as, for example, kneading machines like those normally used for solid or pasty substances. It is also possible for example to use suitable extruders such as, for example, a twin screw extruder. Kneading machines are preferably used as mixing apparatus. The drying can then be carried out directly in the equipment and be carried out to a desired degree of predrying or else to complete drying.

Such apparatuses expediently have suitable control devices to control the product temperature, because the initial neutralization reaction between acid and metal hydroxide may lead to evolution of much heat. The product temperature during the mixing process in the first stage should essentially be, apart from a short initial period, 50° C.-120° C. In a preferred embodiment of the method, the product temperature in the first stage should essentially be 70° C.-120° C. It is preferred first to mix the acid component with the hydroxide component and, after the neutralization reaction, to admix the hygroscopic substance or the carnitine. The product temperature on addition of the hygroscopic substance or the carnitine should be at least 50° C., preferably at least 70° C., during the first stage of the method. The reaction preferably lasts no more than one hour. It is expedient to mix the organic acid and the metal hydroxide in stoichiometric amounts. The combination of heat, finely dispersed solids and a small content of water as solvent leads to a free-flowing, mixable composition.

In a preferred embodiment, L-carnitine, magnesium hydroxide and citric acid are mixed in stoichiometric amounts, i.e. in a molar ratio of approximately 1:1:1. The types of these substances are preferably sufficiently pure, i.e. approved for the manufacture of food products or the preparation of pharmaceuticals, as are described, for example, in the European Pharmacopoeia. Anhydrous types are expediently used. To avoid an unwanted salt loading, the pure L-carnitine is preferably added to the mixture as neutral inert salt. Compared with previous methods of preparation, the hygroscopicity of the complex salt L-carnitine-magnesium citrate prepared in this way is reduced further. For example, the moisture uptake, determined by gravimetry in the way familiar to the skilled worker, of solid carnitine-Mg citrate prepared by the method of the invention and previously dried to constant weight under oil-pump vacuum or over phosphorus pentoxide is not more than 7% by weight after 48 h at 56% relative humidity (rH). This figure is not exceeded even after storage for 330 h. Based on the amount of carnitine or carnitine derivative present in the mixture, referred to within the scope of the invention as carnitine content based on free base, this corresponds to a moisture uptake of not more than 40% by weight. It is preferred for at least 80% of the carnitine-Mg citrate, based on the carnitine content in the mixture, to be in the form of complex salt in the mixture of the invention.

It is also possible, in a further preferred embodiment, to prepare a complex salt from carnitine, magnesium hydroxide and hydroxycitric acid (HCA). Hydroxycitric acid is described in detail hereinafter in this description. HCA has a special function as agent promoting breakdown of fats. Such a combination is particularly advantageous because the advantageous material properties of the complex salt is associated with the synergistic cooperation of the latter's components.

The method of the invention also permits mixtures of salts which crystallize only poorly using known methods, such as, for example, L-carnitine and ascorbic acid, to be prepared.

The reduction of the water content of the pasty mixture preferably takes place by drying in vacuo at a minimum of 85° C., in a most preferred embodiment at a minimum of 90° C., and a maximum of 120° C., and takes place under a pressure extending to 25 mbar, preferably not more than 50 mbar. The drying may, depending on the amount of product, take up to about 3 h. Surprisingly, the composition produced in this way is still, despite its increase in solidification as the water content decreases, flowable or pasty to a very limited extent. For the purposes of the present invention, pasty is thus regarded as a composition which is flowable only under elevated pressure (>1 bar) and at a minimum of 85° C., in the sense of flow characteristics referred to as extrusion viscosity. The pasty composition is movable in the hot state by suitable apparatuses with an adequate torque. Definitive solidification takes place only through cooling. It is possible to expedite the cooling by methods known per se, for example extrusion as thin strand and/or solidification on a cooling belt. It is also possible to add an additional after-drying step during or after the cooling process, for example a further vacuum drying. On use for example of kneading machines with low torque or with a design which is unfavorable for discharge, it may be expedient to discharge the composition while still hot and while still in a viscous state from the mixing apparatus before the first vacuum drying step and only then to undertake the further processing steps according to the method of the invention.

Once the product has solidified it can be coarsely comminuted for further processing and sent for a final granulation or fine granulation. It may in a preferred embodiment of the present method be comminuted to a particle size not exceeding 1 mm using apparatuses known per se to the skilled worker. In a further preferred embodiment, the comminution is carried out with screening granulators (from FREWITT) and, on use of an extruder with suitable die plates, preferably directly on the coarse granules produced by the extruder without an additional interpolated comminution step.

It is also possible to add further active substances to the mixture of the invention during the mixing process in the method of the invention, for example coenzymes such as niacin or niacinamide or other substances which promote growth or the breakdown of fats and which may cooperate synergistically with L-carnitine, such as β-hydroxy-β-methylbutyrates, (−)-hydroxycitrate, lipoic acid or lipotrophic substances such as lecithin or choline. $Ca^{2+}$ like $Mg^{2+}$ are required for muscle activity, so that this results in a suitable synergistic effect with the effect of carnitine or else creatine which promotes muscle activity and energy metabolism.

The present application further relates to a mixture that can be granulated, preferably for dietary supplementation or for pharmaceutical dosage, comprising salts of carnitine, preferably L-carnitine, at least one alkali metal or alkaline earth metal and one physiologically acceptable organic acid, characterized in that the water uptake of the previously dried mixture at a relative humidity of 56° C. under atmospheric pressure and at 25° C. is not more than 15% by weight, preferably not more than 10% by weight, and in a most preferred embodiment not more than 7% by weight, after 24 h, and preferably also after 14 days. Based on the carnitine content of the mixture, the water uptake by the previously dried mixture does not exceed 40% by weight. Drying means in this connection drying over phosphorus pentoxide to constant weight at 25° C. Salts mean in this connection all possible salt compounds between in each case at least two of the substances present in the mixture of the invention. Such a mixture can be prepared by the method of the invention and identifies itself by a particularly low hygroscopicity. Especially with carnitine-magnesium citrate or hydroxycitrate, the latter is further reduced by comparison with the type produced using the previous method of preparation.

Correspondingly, in a preferred embodiment the organic acid or the acid residue present in the mixture is preferably a citrate, a (−)-hydroxycitrate or an ascorbate and, preferably, the alkaline earth metal is calcium, magnesium or a mixture of the two. In addition, the acid residue and the alkaline earth metal cation are, in a preferred embodiment, present in stoichiometrically equivalent amounts. In a further preferred embodiment, the mixture additionally contains at least one other substance from the group consisting of ribose, niacin, niacinamide, β-hydroxy-β-methylbutyrate, lipoic acid, coenzyme Q 10 and chromium(III) salts, for example chromium picolinates or chromium nicotinates.

The present invention further relates to a mixture for dietary supplementation comprising L-carnitine or an alkanoyl carnitine, coenzyme Q and β-hydroxy-β-methylbutyrate and, optionally, (−)-hydroxycitrate. It may also comprise a combination of various carnitine salts including the inner salts or of the carnitine derivatives and the salts thereof. Such a mixture is novel and can likewise be prepared in a solids-mixing method of the invention, for example using an extruder, as mixture that can be granulated. Such a mixture can, however, also be prepared in another known method.

The organic acids present in this mixture may be present in the mixture in the protonated form or as salt with a counterion. In particular, the carnitine or carnitine derivative can be present in the mixture as complex salt or as inner salt or as salt with a counterion. The advantage of such a mixture is the synergistic cooperation of the advantageous properties and physiological functions of the components.

The mixture of the invention comprises both substances which promote burning up of fats or mobilization of the body fat and substances which inhibit the neosynthesis of fat and fatty acids. Such a mixture can be used in particular as dietary supplement assisting the breakdown of body fat or, as part of a diet, as constituent of food substitute preparations or weight-loss agents.

Carnitine, i.e. in its physiologically active form the L-(−) enantiomer, promotes the transport of fat and of the basic metabolic building block acetyl-CoA through cell membranes to the site of utilization in energy metabolism, the mitochondrial matrix. Carnitine thus increases the substance flux during the beta oxidation of fatty acids. Ubiquinone or coenzyme Q, preferably coenzyme Q 10, is another molecule able to cross membranes which is, during the redox processes of oxidative phosphorylation, an important intermediary as electron donor in the mitochondrial membrane and thus in the utilization of the metabolic energy generated by burning of fatty acids. The combination of carnitine and ubiquinone thus represents an advantageous cumulative cooperation of two principles of action. At the same time, the neosynthesis of fatty acids and the utilization of alternative energy sources during the citrate cycle is impeded. (−)-Hydroxycitrate inhibits ATP-citrate lyase. β-Hydroxy-β-methylbutyrate reduces, through substrate inhibition, the availability of acetyl-CoA, the central cofactor in fatty acid and cholesterol biosynthesis. In addition, coenzyme Q has the function, in the mixture stored in the dry, of an antioxidant promoting storage stability. For the purposes of the present invention, "Q10" means the differentiation customary in biochemistry of the biogenic ubiquinones through the length of the isoprenyl side chains, the species with 10 carbon atoms in the side chain being the species which is most frequently represented in most mammals, including humans. However, it is also possible to prepare the mixture of the invention with other ubiquinones physiologically active in humans, as can be obtained for example from microorganisms. For example, the predominant coenzyme Q species in yeast (*S. cerevisiae*) is Q6 (6 carbon atoms).

It is possible to supplement the mixture of the invention with further ingredients which advantageously support the synergistic effect. Such a mixture may comprise at least one or, in any combination, a plurality of substances from the group consisting of vitamin C, lipoic acid, vitamin E, ribose, niacin, niacinamide, creatin and Cr (III) salts, preferably Cr picolinate or Cr nicotinate. The substances are well known from sports and health diets and play either a part in energy metabolism or fat utilization, the mobilization of the body's reserves or, as cellular antioxidants, have a protective function in relation to an increased energy metabolism. In particular, (−)-hydroxycitric acid, which can be obtained as predominant fruit acid from fruits of the genus *Garcinia*, is another component of the mixture in the most preferred embodiment.

Preferred practical embodiments of the mixture of the invention, and of other salts or mixtures of the present invention, are dosage forms known per se, such as capsules, coated tablets, tablets, injection solutions, effervescent tablets which contain, for example, 10-1 000 mg of carnitine (or a derivative), 10-1 000 mg of coenzyme Q and 10-1 000 mg of β-hydroxy-β-methylbutyrate. For example, a conventional hard gelatin two-piece capsule may contain 300 mg of each of the three substances of the invention, mixed with colors and microcrystalline cellulose as carrier. It is, however, also possible to add these substances in comparable amounts to a suitable portion of a food product, for example cornflakes, energy bars, jam etc.

The present invention further relates to carnitine-magnesium hydroxycitrate. This is a salt of low hygroscopicity and can be prepared by the present method through mixing magnesium hydroxide, hydroxycitric acid and carnitine or alkanoyl carnitine in the molar ratio 1:1:1. It is a neutral salt in the stoichiometric composition, in relation to the charge distribution and the ionizable functional groups. Hydroxycitrate means for the purposes of the present application preferably the (−) enantiomer as described (Lewis, Y. et al., Water extract of (−) Hydroxy-Citric acid from fruit of *Garcinia Cambogia*, Phytochemistry (1965), 4, p. 619-625; Lewis, Y. et al., Acetone extract of (−) Hydroxy-Citric acid from the fruit of *Garcinia Cambogia*. The salt can preferably be used within the meaning of the above statements as weight-loss agent, to promote breakdown of body fat. The use of hydroxycitrate as such as weight-loss agent and suitable dosages are described for example in U.S. Pat. No. 5,783,603. Surprisingly, the novel mixed salt of the invention assists, at least on oral administration, in a surprising, more than just additive, way the occurrence of the desired breakdown of fats and weight loss. This involves a synergistic effect of the mixture in the form of a complex salt. Without wishing to be bound to the theory, it is possible that this effect is brought about by a better bioavailability of the complex salt. HCA is prone to spontaneous lactonization in aqueous solution and in the gastrointestinal tract. The complexation with Mg before preparation of a solution might have a stabilizing effect in relation to the unwanted rearrangement of the lactone and thus bring about much greater activity in cooperation with carnitine. The salt of the invention at least shows an improved storage stability, in relation to the rearrangement of HCA to the lactone, compared with known HCA salts under standard test conditions customary in the pharmaceutical sector. It is also possible that a previously unrecognized stimulating effect in particular of magnesium, in the sense of that stated above concerning the mechanism of action of carnitine and hydroxycitrate, is involved. Allosterically regulated enzymes are often regulated by various factors such as, for example, also Mg cations. Magnesium is moreover an important cofactor for various enzymes or constituent of the holo enzyme. It is possible that the enzyme systems which are important for carnitine and hydroxycitrate, or are influenced thereby, are subject to a simultaneous synergistic control by magnesium ions.

Hydroxycitric acid (HCA) activates indirectly carnitine palmitoyltransferase I (CPT) through suppression of the synthesis of malonyl CoA. Malonyl CoA is an important allosteric inhibitor of this enzyme. CPT is important for the transport function of carnitine for fatty acids through the mitochondrial membrane and may, if the activity is inadequate, be limiting for carnitine-mediated transport and thus for fatty acid oxidation in the mitochondria. In addition, malonyl CoA is a direct precursor for the biosynthesis of fatty acids and cholesterol.

The site of action of HCA is the enzyme citrate lyase which is competitively inhibited by HCA. The affinity of the enzyme for HCA is more than 100 times higher than for the natural metabolic substrate citric acid. The lactone derivative to which HCA spontaneously cyclizes has a clear lower affinity by comparison.

Preferred practical implements of the mixture of the invention are dosage forms known per se, such as capsules, coated tablets, tablets, injection solutions, effervescent tablets which contain for example 10-2000 mg of carnitine-magnesium hydroxycitrate. For example, a conventional hard gelatin two-piece capsule may contain 1000 mg of carnitine-magnesium hydroxycitrate mixed with colors and microcrystalline cellulose as carrier. It is, however, also possible to add the substance of the invention in comparable amounts to a suitable portion of a food product, for example cornflakes, energy bars, jam etc. It is also possible to use carnitine-magnesium hydroxycitrate mixed with β-hydroxy-β-methylbutyrate or other aforementioned substances.

EXAMPLES

Example 1

Preparation of L-Carnitine-Magnesium Citrate 128 g of anhydrous citric acid and 39 g of $Mg(OH)_2$ pharm. are mixed in a kneader for small batches (HKD-T 0.6 IKA) with 36 g of deionized water (water content based on complete mixture: 11.6%) while heating to 73° C. for 40 min. 107.5 g of L-carnitine are then added thereto and kneading is continued at 49-50 rpm for 35 min until a gummy white consistency results. After drying in vacuo at 90° C. for 4 h, the composition is dry and hard. The product is checked by IR and polarimetry and is very pure. The product dissolves in water without residue. The water content of the dried substance is 10.1% by weight.

Example 2

Preparation of L-Carnitine-Magnesium Citrate 134 g of anhydrous citric acid and 38.5 g of $Mg(OH)_2$ pharm. are initially mixed in a centrifugal force mill for 7 min and then mixed together with 36 g of deionized water (water content based on complete mixture: 11.4%) in a kneader for small batches (HKD-T 0.6 IKA) while heating to 79° C. for 30 min. 107.5 g of L-carnitine are then added thereto, and kneading is continued at 40-50 rpm for 45 min until homogeneous. After drying in vacuo at 90° C. for 4 h, the composition is dry and hard. The product is checked for purity by IR and polarimetry and gives a clear solution in water. The water content of the dried substance is 8.8% by weight.

Example 3

Hygroscopicity Test

The product mixtures from example 1 and 2 granulated to a particle size of <0.8 mm using a FREEWIT screening granulator are stored at a relative humidity of 56% at 25° C. under constant test conditions for the stated times. The sample was previously dried to constant weight over phosphorus pentoxide. The moisture uptake from the air is determined by gravimetry. The weight gain is stated in percent based on the total weight of the sample. Conventional L-carnitine-magnesium citrate from the production method of EP 402 755, which has been press-granulated to the same particle size, serves as reference sample and is comparable in terms of the particle properties (flow, low dust).

| Storage time/h | + % by weight reference | + % by weight example 1 | + % by weight example 2 |
| --- | --- | --- | --- |
| 4 | 5.1 | 2.0 | 2.7 |
| 8 | 9.1 | 2.2 | 3.0 |
| 24 | 18.1 | 4.6 | 5.4 |
| 36 | 17.6 | 4.4 | 5.5 |
| 48 | 20.4 | 5.2 | 6.4 |
| 336 | 15.6 | 5.1 | 6.5 |

Example 4

Preparation of L-Carnitine-Magnesium (−)-Hydroxycitrate

Preparation takes place in the method described in example 2, mixing 83 g of carnitine (free base), 137 g of (−)-hydroxycitric acid HCA-650 77.7%, 30 g of Mg hydroxide and 55 g of water.

The weight gain of the mixture of the invention which had previously been dried was, after 24 h under standard conditions, 0.82% by weight. At a relative humidity of 56%, the water uptake of the mixture determined by gravimetry was ≦10% by weight after 30 h, corresponding to about 30% by weight based on the carnitine content of the mixture.

The invention claimed is:

1. Carnitine-magnesium hydroxycitrate, that is a salt compound and that has a molecular ratio of the magnesium, the carnitine and the hydroxycitrate of 1:1:1, said carnitine-magnesium hydroxycitrate, having been dried to constant weight, has a moisture uptake of 7 weight percent or less, based on said carnitine-magnesium hydroxycitrate, after 48 hours at 56 percent relative humidity.

2. The carnitine-magnesium hydroxycitrate as claimed in claim 1, wherein the carnitine is L-carnitine.

3. The carnitine-magnesium hydroxycitrate as claimed in claim 1, wherein the carnitine-magnesium hydroxycitrate is a solid.

4. The carnitine-magnesium hydroxycitrate as claimed in claim 3, wherein the carnitine is L-carnitine.

5. The carnitine-magnesium hydroxycitrate as claimed in claim 1, wherein the carnitine-magnesium hydroxycitrate is pasty.

6. The carnitine-magnesium hydroxycitrate as claimed in claim 5, wherein the carnitine is L-carnitine.

7. The carnitine-magnesium hydroxycitrate, that is a salt compound and that has a molecular ratio of the magnesium, the carnitine and the hydroxycitrate of 1:1:1, wherein the carnitine-magnesium hydroxycitrate has been prepared by the method comprising:
   (a) in a first stage, mixing carnitine, magnesium hydroxide and hydroxy-citric acid, without addition of water or with addition of no more than 15 percent by weight of water based on the weight of the complete mixture containing the carnitine-magnesium hydroxycitrate; and
   (b) in a second stage, reducing the water content of the complete mixture by drying to below 5 percent by weight, with the carnitine-magnesium hydroxycitrate being obtained.

8. Composition comprising carnitine-magnesium hydroxycitrate, that is a salt compound and that has a molecular ratio of the magnesium, the carnitine and the hydroxycitrate of 1:1:1.

9. The composition according to claim 8, wherein the carnitine-magnesium hydroxycitrate is L-carnitine.

10. The composition according to claim 8, wherein the carnitine-magnesium hydroxycitrate is a solid.

11. The composition according to claim 10, wherein the carnitine-magnesium hydroxycitrate is L-carnitine.

12. The composition according to claim 8, wherein the carnitine-magnesium hydroxycitrate is pasty.

13. The composition according to claim 12, wherein the carnitine-magnesi um hydroxycitrate is L-carnitine.

14. The carnitine-magnesium hydroxide as claimed in claim 3, wherein the solid carnitine-magnesium hydroxide is in the form of coarse granules or fine powder.

15. The carnitine-magnesium hydroxycitrate as claimed in claim 7, wherein the carnitine is L-carnitine.

16. The carnitine-magnesium hydroxycitrate as claimed in claim 7, wherein the carnitine-magnesium hydroxycitrate is a solid.

17. The carnitine-magnesium hydroxycitrate as claimed in claim 16, wherein the carnitine is L-carnitine.

18. The carnitine-magnesium hydroxycitrate as claimed in claim 7, wherein the carnitine-magnesium hydroxycitrate is pasty.

19. The carnitine-magnesium hydroxycitrate as claimed in claim 18, wherein the carnitine is L-carnitine.

* * * * *